(12) United States Patent
Vielhaber et al.

(10) Patent No.: US 8,354,128 B2
(45) Date of Patent: Jan. 15, 2013

(54) BLACKBERRY LEAF EXTRACT AS AN ACTIVE INGREDIENT AGAINST SKIN IRRITATIONS AND INFLAMMATIONS

(75) Inventors: Gabriele Vielhaber, Holzminden (DE); Martina Herrmann, Hameln (DE); Imke Meyer, Bodenwerder (DE); Holger Joppe, Dassel (DE)

(73) Assignee: Symrise AG, Holzminden (DE)

( * ) Notice: Subject to any disclaimer, the term of this patent is extended or adjusted under 35 U.S.C. 154(b) by 524 days.

(21) Appl. No.: 12/095,679

(22) PCT Filed: Nov. 30, 2006

(86) PCT No.: PCT/EP2006/069090
§ 371 (c)(1),
(2), (4) Date: Jun. 9, 2010

(87) PCT Pub. No.: WO2007/063087
PCT Pub. Date: Jun. 7, 2007

(65) Prior Publication Data
US 2010/0239695 A1    Sep. 23, 2010

Related U.S. Application Data

(60) Provisional application No. 60/741,453, filed on Dec. 2, 2005.

(51) Int. Cl.
*A61K 36/73* (2006.01)
(52) U.S. Cl. ........................ 424/765; 424/774
(58) Field of Classification Search ............... None
See application file for complete search history.

(56) References Cited

U.S. PATENT DOCUMENTS

| 7,709,031 B2 * | 5/2010 | Greenway et al. ............ 424/725 |
| 2003/0203054 A1 | 10/2003 | Selzer et al. |
| 2008/0095719 A1 * | 4/2008 | Herrmann et al. ............ 424/48 |

FOREIGN PATENT DOCUMENTS

| JP | 09118627 A * | 5/1997 |
| WO | WO 02/38537 A1 | 5/2002 |
| WO | WO-2005000330 | 1/2005 |
| WO | WO-2005123101 | 12/2005 |

OTHER PUBLICATIONS

Ito et al. "Degradation of Interleukin 1 beta by Matrix Metalloproteinases", Journal of Biological Chemistry, vol. 271, No. 25, pp. 14657-14660, 1996.*
Database WPI Week 199020, Derwent Publications Ltd., London, GB; and 1990-153092, XP002423944 & RO 97 734 A (Pasteur Inst Veterinare) Sep. 30, 1989, abstract.
Database Biosis [Online] Biosciences Information Service, Philadelphia, PA, US; 1992, Yasuda Hideyuki et al: "Deodorant effect of plant extracts of the family Rosaceae against methyl mercaptan," XP002423934, Database accession No. PREV199935053863, abstract & Nippon Nogeikagaku Kaishi, vol. 66, No. 10, 1992, pp. 1475-1479, ISSN: 0002-1407.
Rubi fruticosi folium (Brombeerblätter). Erscheinungsdatum Bundesanzeiger: Jan. 2, 1990. Heftnummer: 22a. ATC-Code A07XA. Monographic BGA/BfArM (Kommission E). http://buecher.heilpflanzen-welt.de/BGA-Kommission-E-Monographien.
Reilly, D. M. et al. Eicosanoid and Cytokine Levels in Acute Skin Irritation in Response to Tape Stripping and Capsaicin. Acta Derm Venereol (Stockh) 1999; 79: 187-190.
Misery, L. et al. Peaux sensibles en France: approche épidémiologique. Articles scientifiques. Memoire original. English Language Summary included. pp. 425-429.
Kydonieus, Ph.D., Agis F. et al. Biochemical Modulatuion of Skin Reactions: Transdermals, Topicals, Cosmetics. CRC Press. Kopie von subito e.V., geliefert für Symrise AG (DTL9800126). pp. 124-143. (2000).

* cited by examiner

*Primary Examiner* — Christopher R. Tate
*Assistant Examiner* — Deborah A. Davis
(74) *Attorney, Agent, or Firm* — Connolly Bove Lodge & Hutz LLP

(57) ABSTRACT

The present invention concerns the field of plant extracts and their uses, in particular for cosmetic, oral hygiene and pharmaceutical purposes. In particular the invention concerns blackberry leaf extracts and preparations and medicaments containing them, as well as their use to inhibit irritating and inflammatory skin conditions.

8 Claims, 1 Drawing Sheet

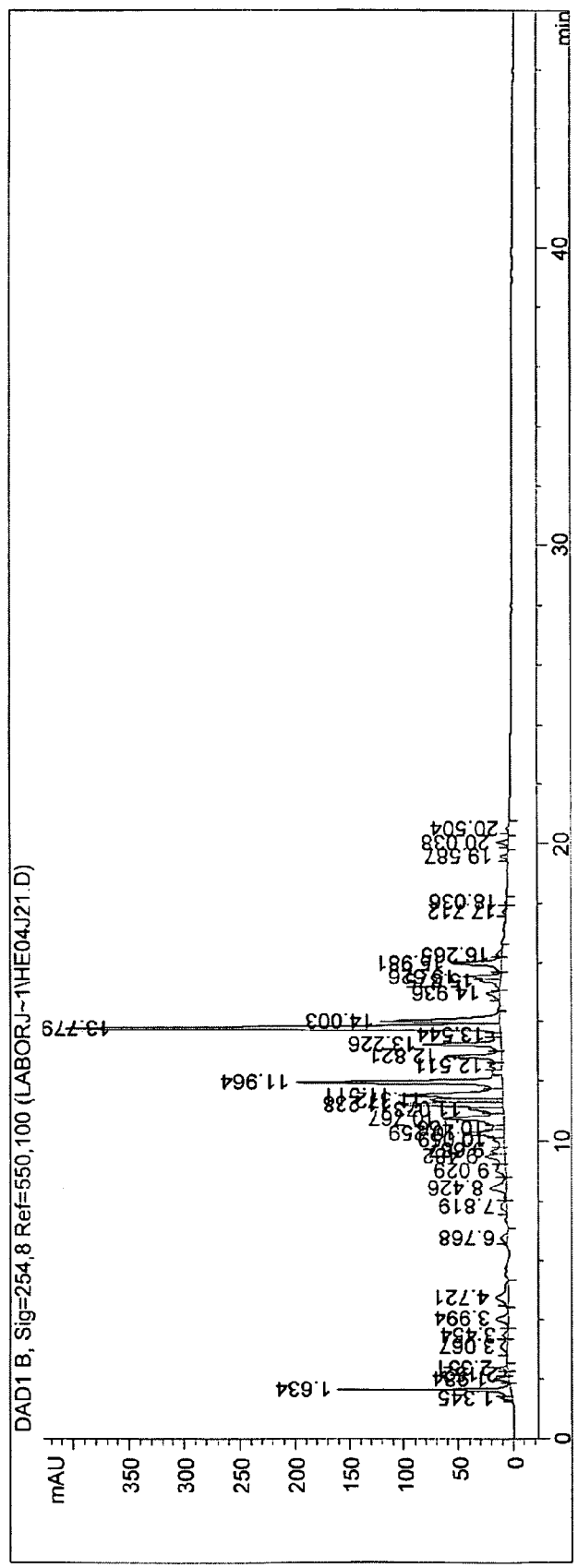

BLACKBERRY LEAF EXTRACT AS AN ACTIVE INGREDIENT AGAINST SKIN IRRITATIONS AND INFLAMMATIONS

CROSS-REFERENCE TO PREVIOUS APPLICATIONS

The present application claims benefit of PCT/EP2006/069090 filed on Nov. 30, 2006, which claims benefit of U.S. Provisional Application 60/741,453 filed on Dec. 2, 2005, the disclosures of which are incorporated by reference herein in their entirety.

DISCLOSURE

The present invention concerns the field of plant extracts and their uses, in particular for cosmetic, oral hygiene and pharmaceutical purposes. In particular the invention concerns blackberry leaf extracts and preparations and medicaments containing them, as well as their use to inhibit irritating and inflammatory skin conditions.

It also concerns a medicament for the treatment of skin irritations and inflammations and the use of such a preparation or such a medicament for the prevention of skin irritation and inflammations and/or the treatment of skin irritations and inflammations for medical and/or non-medical purposes.

It concerns furthermore a process for the production of a preparation or medicament having a skin irritation-reducing and anti-inflammatory effect, a cosmetic or therapeutic process for the prevention and one for the treatment of skin irritations and inflammations, a process for the prevention of the skin-irritant effect and a process for the reduction, relief or suppression of the skin-irritant and anti-inflammatory effect of a substance or mixture of substances and a kit comprising a preparation having a skin irritation-reducing and anti-inflammatory effect.

In the cosmetic and pharmaceutical industry there is an ongoing need for agents having a skin irritation-reducing effect.

As the barrier organ of the human organism, the skin, and especially the epidermis, is particularly subject to external influences. Many intrinsic (e.g. genetic disposition) and extrinsic (e.g. damage to the skin barrier, exposure to UV light, irritating or allergy-triggering substances) factors can lead to a skin irritation and—in severe cases—to a subsequent skin inflammation. Within the context of this application, skin irritation is understood to be any change in the skin which in humans or animals triggers sensorial discomfort or/and is marked by a dry, reddened and/or inflamed appearance of the skin. The term sensorial discomfort naturally also includes conditions such as itching or pain. Skin irritation can include in particular phenomenologically differing skin conditions: sensitive skin, delicate skin, including a delicate scalp, vulnerable skin, atopic skin, irritated skin, inflamed skin, which in more severe cases is expressed by a reddening of the skin known as erythema.

The problem of "sensitive skin" affects a growing number of adults and children. It is now assumed that up to 50% of the population have a sensitive skin (L. Misery et al., Ann. Dermatol. Venereol. 2005, 132, 425-429). Sensitive skin denotes a skin having a reduced irritation threshold for irritants, such as hyperreactive, intolerant and also atopic skin. A phenomenon described as stinging can be observed in people having a sensitive, delicate or vulnerable skin. Typical disruptive phenomena associated with the terms stinging or sensitive skin are reddening of the skin, tingling, prickling, tightness and burning of the skin and itching. They can be provoked by stimulating environmental conditions such as e.g. massage, the effect of surfactants, weather influences such as heat, cold, dryness, but also humid heat, heat radiation and UV radiation, from the sun for example, or by psychological stress.

A "delicate" scalp is likewise characterised by reddening of the skin, tingling, prickling, burning and itching. Triggers are, for example, soap, shampoos or other hair care products, surfactants, hard water having a high concentration of lime and/or mechanical stresses. Erythema and hyperseborrhoea (excessive sebum production) of the scalp as well as dandruff are commonly associated with the phenomena described.

A phenomenon observed in around 10 to 20% of the population of industrial countries and one which is on the increase is a familial oversensitivity of the skin and mucous membranes to environmental substances, with an increased tendency to develop immediate oversensitivity reactions (allergies) to substances from the natural environment. Atopia is assumed to be a genetic condition. Atopia can also manifest itself as atopic dermatitis. Here the skin barrier is damaged, the skin is often inflamed and itches.

The erythematous effect of the ultraviolet portion of solar radiation or artificial radiation on the skin is generally known. Whilst rays having a wavelength of less than 290 nm (known as the UVC range) are absorbed by the ozone layer in the earth's atmosphere, rays in the range between 290 nm and 320 nm, the UVB range, cause an erythema, a simple sunburn or even more or less severe burns.

Erythematous skin phenomena also arise as side effects of certain skin conditions or irregularities. For example, the typical skin eruption that appears with acne is generally reddened to a greater or lesser degree and even in mild cases has a detrimental effect on the well-being of the sufferer.

Erythemas are also more common in the nappy region of small children and even more so in infants (nappy rash). Incontinence too, a complaint that is especially prevalent in old age, is commonly associated with erythemas and skin reddening as a result of constant exposure to moisture and irritants (incontinence dermatitis).

Periodontitis is an inflammation of the periodontium, in other words the tissues that surround and support the teeth. The periodontium comprises various tissues: the gum epithelium (gingiva), the connective tissue of the gingiva, the periodontal ligament (desmodontium), the cementum and the surrounding alveolar bone. The desmodontium is located between the surface of the root and the alveolar bone. It is a cell-rich connective tissue which holds the tooth in the bony tooth socket, the alveolus. 53 to 74% of the periodontal space is made up of collagen and oxytalan fibre bundles. The portion of the periodontal fibres incorporated into the cementum and the alveolar bone holds the tooth in the alveolus. The main clinical features of periodontitis include inflammation of the gums, attachment loss, formation of periodontal pockets and degradation of the alveolar bone.

The main cause of periodontitis is plaque. This consists of certain components of saliva, food residues and above all bacteria and their decomposition products. This special form of an infectious disease is caused in most cases by *Porphyromonas gingivalis, Bacteroides forsythus* and *Actinobacillus actinomycetemcomitans*. The continuous release of bacterial toxins, especially of lipopolysaccharides, presumably triggers the release of proinflammatory mediators, such as e.g. IL-1 beta particularly from interleukins, TNF-alpha and PGE2, in the patient's affected tissues. These signal substances stimulate the infiltration of immunocompetent cells into the populated tissue. The migration of neutrophilic granulocytes and macrophages then subsequently leads to inflammation of the gums (gingivitis) and to the release of proinflammatory mediators such as IL-1 and IL-6, for example. These in turn activate in the skin and mucous membranes the synthesis of matrix-degrading metalloproteinases (matrix metalloproteinases, MMPs), which destroy the extracellular matrix of the surrounding connective tissue. This allows bacteria, which initially interacted with the free gingiva, to penetrate further into the underlying connective tissue, continuing inflammation processes there and finally loosening the connection between the uppermost layer of the epithelium and the root of the tooth. A gingival pocket is formed as a consequence. The reaction of the body is the inflammation of the gingiva and the periodontium with damage to the alveolar bone. In the final stage of periodontitis the affected person is at risk of a massive loss of teeth.

Dental pulp (pulpa) too can be affected by inflammatory processes caused by caries. The teeth are constructed mainly from a bonelike substance called dentine. In the area of the crown which protrudes from the gum, the dentine is covered with protective enamel.

Caries is caused by the bacteria in the plaque on the surface of the tooth. Bacteria such as *Streptococcus mutans* and *Lactobacillus casei* convert sugars and food residues into acid, which attacks and destroys tooth enamel and dentine. The continually multiplying, acid-forming plaque bacteria penetrate through holes in the enamel along the canals that pass through the dentine towards the dental pulp (pulpa), leading to inflammation. In addition to bacteria, chemicals or mechanical damage can also cause irritation or an inflammation reaction in the gums or oral mucosa. Proinflammatory mediators, especially interleukins such as e.g. IL-1alpha and PGE2, are released in this process (Reilly, D. M. and M. R. Green (1999) Eicosanoid and cytokine levels in acute skin irritation in response to tape stripping and capsaicin, Acta Derm Venereol 79 (3) 187-90). IL-1alpha is particularly important here, since this cytokine occurs in the skin in a hundred to a thousand times larger amounts than in other tissue and thanks to its broad chemotactic effect on immune cells is one of the principal initiators of the inflammation reaction cascade (Coquette, A., N. Berna, Y. Poumay and M. Pittelkow, The Keratinocyte in Cutaneous Irritation and Sensitization, 125-143).

In the Commission E monograph, blackberry leaves in the form of aqueous tea infusions and mouthwashes are indicated inter alia for the area of application of mild inflammations of the mucous membranes of the mouth and pharynx (Bundesanzeiger, 1.2.1990, issue number 22a, no. 01071). The effectiveness is attributed to the astringent effect of the tannins they contain. There is no information however on the treatment of skin irritations and on the inhibition of interleukin releases.

Although large numbers of active ingredients having a skin irritation-reducing effect are already used in the claimed technical areas, alternatives are still sought. In the context of this text, skin irritation-reducing effect is understood to be the moderation, reduction, halting or prevention of skin irritations, in particular that of the skin phenomena described above. The skin irritation-reducing effect is based in particular here on calming of the skin, inhibition of inflammation and/or relief of reddening. The term "skin" in this text also covers the term "mucous membranes". In the search for alternative agents, however, it must be taken into account that the substances used must be non-toxic, highly compatible with the skin and stable (especially in the conventional cosmetic and/or pharmaceutical formulations), must have as little inherent odour and as little natural colour as possible and be able to be produced at low cost. In line with the ongoing trend towards natural active ingredients, novel active ingredients of a natural, especially plant, origin are sought in particular.

Surprisingly it has been found in extensive in-house investigations that an alcoholic extract of the leaves of blackberries (*Rubus fruticosus*) exhibits an outstanding skin irritation-reducing and anti-inflammatory effect.

According to the invention a preparation is thus provided comprising or consisting of a blackberry leaf extract in a sufficient concentration to inhibit and/or relieve a skin irritation and/or inflammation and/or in a sufficient concentration to reduce the release of an interleukin, the blackberry leaf extract being obtained by or obtainable by a process comprising the following steps:
a) Addition to blackberry leaves of an extractant containing an alcohol selected from the group consisting of methanol, ethanol, n-propanol, iso-propanol and mixtures of two or more of these alcohols, and
b) Extraction of the blackberry leaves with the extractant for up to 72 hours.

Preparations obtained in this way have proved to have particularly good skin irritation-reducing and anti-inflammatory properties, even in low concentrations. Surprisingly, the preparations are also more effective for reducing and inhibiting skin irritations and inflammations than conventional aqueous blackberry leaf extracts. Where mention is made below of an "extract according to the invention", it always also includes a preparation according to the invention and a medicament according to the invention. The preparation can in particular be a medicament or a non-pharmaceutical, for example a cosmetic, preparation.

Dried blackberry leaves are preferably used. It is also preferable to use only blackberry leaves for the extraction and not also other plant parts such as the berries of the blackberry or its branches and roots.

A further advantage of the preparation according to the invention and thus also of its production process according to the invention is that the preparation can be largely or completely decolourised with conventional chlorophyll removal methods, for example by the addition of activated carbon or bleaching clay directly during extraction or in a subsequent step, without its losing its skin irritation-reducing and anti-inflammatory effect. The extract additionally exhibits only a slight inherent odour. Both features are particularly advantageous in cosmetics and above all in the area of leave-on products, since the extract according to the invention thus leads to little or no change in the appearance and odour of a cosmetic preparation containing the extract even in high concentrations.

Particularly preferred extracts can be obtained with extractants which contain ethanol as the alcohol component. These extractants, unlike methanol-containing types for example, are comparatively safe to use and easy to obtain in a technically adequate grade. In particularly preferred processes and for the production of correspondingly preferred extracts, the extractant contains only one alcohol, preferably ethanol. The person skilled in the art is aware that, particularly when technical alcohol is used, other constituents can also be contained in the extractant as impurities; such impurities are not important for the success of the process according to the invention.

The ratio of the mass of extractant to leaf solids is preferably established such that at least a 10-fold mass of extractant relative to the leaf solids and preferably no more than a 50-fold mass of extractant relative to the leaf solids is obtained, preferably a 10- to 20-fold mass. A 14- to 18-fold mass of extractant relative to the leaf solids is particularly preferably used for extraction. Good results were achieved with a 16-fold mass of an ethanol-containing solvent (relative once again to the leaf solids).

The extraction time for performing step b) is at most 72 hours but can also be shorter. With particularly short extraction times only a very dilute extract is obtained in step b). It is therefore preferable to extract the blackberry leaves in step b) for at least 1 hour, in particular for at least 2 hours. The extraction time needed to obtain an extract for use in producing cosmetic, oral hygiene and/or pharmaceutical preparations or medicaments is preferably at most 24 hours and particularly preferably at most 4 hours. The necessary extraction time is chosen on the basis of the quality of the blackberry leaves to be extracted, particularly their age, and of the other extraction conditions, particularly the extraction temperature. At high extraction temperatures, in particular at an extraction temperature of 80 to 100° C., the extraction time is preferably 1 h to 6 h and particularly preferably 2 h to 4 h.

In addition, it is particularly preferable to perform the extraction in step b) by refluxing the extractant, particularly at extraction temperatures of 80 to 100° C. In this case the extraction time is preferably no more than 24 hours, extracts having a readily usable composition for use in producing cosmetic, oral hygiene and/or pharmaceutical preparations or medicaments being obtained with an extraction lasting just 2 to 4 hours.

The extraction temperature is established on the basis of the extractant that is used. If an ethanol-containing solvent is used, an extraction temperature of 80° C. to 100° C. is preferred, particularly if a mixture of ethanol and water is used as the extractant, see immediately below in this regard.

It is preferable if the extractant contains the alcohol, particularly ethanol, in a proportion of at least 20 wt. %, based on the total extractant. It is likewise preferable if the extractant contains water in a proportion of at least 15 wt. %, based on the total extractant. It is particularly preferable if the extractant simultaneously contains both at least 20 wt. %, based on the total extractant, of an alcohol (preferably ethanol) and water in a proportion of at least 15 wt. %, based on the total extractant. Surprisingly it was established that pure water or ethanol extracts and corresponding preparations according to the invention demonstrated a lower anti-inflammatory effect than extracts produced using ethanol/water blends. Particularly preferred preparations (blackberry leaf extracts) are obtained with an extractant consisting of ethanol and water in the ratio of 2:8 (2 parts by weight of ethanol mixed with 8 parts by weight of water) to 8:2, preferably in the ratio of 3:7 to 7:3 and particularly preferably in the ratio of 3:7 to 1:1. This applies in particular if the blackberry leaf extract according to the invention or a preparation containing the extract is to be used to inhibit inflammation.

The blackberry leaf extract according to the invention can preferably be processed further to form a blackberry leaf extract according to the invention or a preparation according to the invention, in particular a cosmetic or pharmaceutical preparation, in solid form, by extending the production process according to the invention by means of the following steps:

c) Addition to the extract of a solid carrier which is acceptable for pharmaceutical, oral hygiene and/or cosmetic purposes, and d) Drying of the extract with the added carrier to a residual content of extractant of at most 5 wt. %, based on the total weight of the extract obtained in step d).

Step c) can also be omitted according to the invention, in which case a more highly concentrated powder is obtained than if a carrier is added which is acceptable for pharmaceutical, oral hygiene and/or cosmetic purposes. A solid which is acceptable for pharmaceutical, oral hygiene or cosmetic purposes is one which is at least non-toxic for the organism on which it is to be used. A preferred cosmetically acceptable solid is powdered maltodextrin or glucose.

Particularly preferred according to the invention is a production process and correspondingly a preparation (i.e. a blackberry leaf extract) wherein the extract obtained in step b), optionally together with a carrier which is acceptable for pharmaceutical, oral hygiene and/or cosmetic purposes, such as preferably maltodextrin and/or glucose, is processed further by spray drying to form a powder. Extracts according to the invention having a long shelf life can be produced in this way. In addition, the final concentration of the active ingredients contained in the extract powder can advantageously be easily adjusted by adjusting the mixing ratio of the extract obtained in step b) and the carrier that is acceptable for pharmaceutical, oral hygiene and/or cosmetic purposes. A preferred blackberry leaf extract according to the invention in powder form is produced by mixing maltodextrin and the liquid native blackberry leaf extract obtained in step b) in a mixing ratio of 10 parts by weight of native extract to 90 parts by weight of maltodextrin. "Native extract" refers here to the extract that is obtained when the extractant is eliminated from the extract obtained in step b).

The solid or liquid blackberry leaf extract can moreover also be processed further according to the invention to form a liquid preparation, by mixing the blackberry leaf extract with a solvent chosen from the group consisting of glycerol, 1,2-propylene glycol, 1,3-butylene glycol, ethanol, water and mixtures of two or more of the cited solvents with water. Such extracts or preparations produced according to the invention are particularly readily able to be processed further for cosmetic purposes. These preparations according to the invention can optionally be produced with the addition of a preservative, solubiliser or antioxidant.

Blackberry leaf extract can advantageously be used anywhere in cosmetics where cosmetically desirable effects are linked to inflammation inhibition. The preparation according to the invention is preferably used for the inhibition and/or relief of a skin irritation and/or inflammation. To this end it is preferably applied topically to the skin to be treated.

The invention also covers a medicament for the inhibition and/or relief of skin irritations and/or inflammations, comprising or consisting of a preparation according to the invention having an irritation-reducing effect. Such a medicament can be used in the field of human and veterinary medicine to combat many diseases, such as e.g. urticaria, contact dermatitis, atopia and generally all inflammation processes, as well as tooth or gum inflammations such as periodontitis.

Also preferred is the use of a preparation according to the invention for the (pharmaceutical or non-pharmaceutical, for example cosmetic) reduction of the release of an interleukin. Surprisingly, with the preparations according to the invention it is possible to inhibit the specific release of interleukins (in particular IL1 interleukin), whilst the release of other proinflammatory mediators remains largely uninfluenced. The preparation according to the invention preferably also contains further anti-irritants. Anti-irritants within the meaning of the present invention are anti-inflammatory active ingredients or active ingredients to relieve reddening and itching that are suitable for or commonly used for cosmetic and/or dermatological applications. Substances which reduce the amount of cytokines, interleukins, prostaglandins and/or leukotrienes in cells and tissue are preferred.

Substantial areas of application of cosmetic preparations according to the invention, in particular dermatological preparations, which (except for the presence of blackberry leaf extract) have a conventional composition and are used for cosmetic, particularly dermatological, protection against light, for the treatment, care and cleansing of the skin and/or hair or as a makeup product in decorative cosmetics. Such preparations, depending on their structure, can accordingly be used as, for example, a skin care cream, day or night cream, eye cream, sunscreen or after-sun lotion, skin food, conditioning mask, gel pads, face lotion, moist conditioning and cleansing cloths, cleansing milk, cleansing soap, foam bath or shower gel, deodorant, antiperspirant, shampoo, hair care product, hair conditioner, hair colorant, hair styling product and preferably take the form of an emulsion, lotion, milk, fluid, cream, hydrodispersion gel, balm, spray, alcoholic or aqueous/alcoholic solution, foam, powder, liquid soap, soap bar, shampoo, roll-on, stick or makeup. In hair treatment products the use is preferably directed towards the scalp or intracutaneo-sebaceous hair system.

The concentration of blackberry leaf extract or of a solid or liquid preparation containing blackberry leaf extract in cosmetic, oral hygiene and/or pharmaceutical preparations (especially for topical application) is preferably in the range from 0.00001 to 20 wt. %, preferably in the range from 0.0001 to 5 wt. % and particularly preferably in the range from 0.001 to 5 wt. %.

The blackberry leaf extract used according to the invention can be incorporated without difficulty into common cosmetic or dermatological formulations such as pump sprays, aerosol sprays, creams, ointments, tinctures, lotions, nail care products and the like. It is also possible and in some cases advantageous in this respect to combine the blackberry leaf extract used according to the invention with other active ingredients, for example with active ingredients to combat skin ageing and wrinkles. The cosmetic and/or dermatological formulations containing blackberry leaf extract can otherwise have a conventional composition and be used to treat the skin and/or hair in the sense of a dermatological treatment or a treatment in the sense of conditioning cosmetics. They can also be used in makeup products in decorative cosmetics, however.

Cosmetic preparations according to the invention containing a blackberry leaf extract according to the invention can also contain active ingredients and combinations of active ingredients to combat skin ageing and wrinkles. All active ingredients that are suitable for or commonly used for cosmetic and/or dermatological applications to combat skin ageing and wrinkles can be used here according to the invention. Advantageous active ingredients in this respect to combat skin ageing and wrinkles are soya protein or protein hydrolysates, soya isoflavones, hydrolysed rice protein, hydrolysed hazelnut protein, wheat protein, β-glucanes e.g. from oats and derivatives thereof, glycoproteins, ursolic acid and salts thereof, betulin, betulinic acid and salts thereof, retinol, retinol palmitate, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran, creatine or other synthetic or natural active ingredients to combat skin ageing and wrinkles, wherein the latter can also be used in the form of an extract from plants, such as e.g. green tea, *Sanguisorba officinalis*, *Centella asiatica*, *Ribes nigrum*, *Passiflora incarnata*, *Phyllanthus emblica*, evening primrose, rosemary, sage, echinacea, birch, apple or soya.

Particularly preferred for use as additional active ingredients to combat skin ageing are β-glucane, 1,3-1,4-coupled β-glucane from oats or wheat protein being especially preferred.

For use, the cosmetically and/or dermatologically active blackberry leaf extract is applied to the skin and/or the hair in an adequate amount in the conventional way for cosmetics and dermatological products. Cosmetic and dermatological preparations which contain an extract according to the invention and also act as a sunscreen offer particular advantages here. These preparations advantageously contain at least one UVA filter and/or at least one UVB filter and/or at least one inorganic pigment. The preparations can be in various forms, such as are conventionally used for sunscreen preparations, for example. Thus for example they can form a solution, a water-in-oil (W/O) or oil-in-water (O/W) emulsion, or a multiple emulsion, of the water-in-oil-in-water (W/O/W) type for example, a gel, a hydrodispersion, a solid stick or an aerosol.

As mentioned, preparations containing blackberry leaf extract can particularly advantageously be combined with substances which absorb or reflect UV radiation, the total amount of filter substances being from 0.01 wt. % to 40 wt. %, preferably 0.1% to 10 wt. %, in particular 1.0 to 5.0 wt. %, based on the total weight of the preparations, in order to provide cosmetic preparations which protect the hair or skin from ultraviolet radiation. These preparations advantageously contain at least one UVA filter and/or at least one UVB filter and/or at least one inorganic pigment, such that a light protection factor of at least >2 (preferably >5) is obtained. These preparations according to the invention can be in various forms, such as are conventionally used for sunscreen preparations, for example. Thus they can for example be a solution, a water-in-oil (W/O) or oil-in-water (O/W) emulsion, or a multiple emulsion, of the water-in-oil-in-water (W/O/W) type for example, a gel, a hydrodispersion, a solid stick or an aerosol.

Advantageous UV filters are, for example:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomethyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-ethylhexyl-2-cyano-3,3-diphenyl acrylate (Neo Heliopan®303)
ethyl-2-cyano-3,3'-diphenyl acrylate
2-phenylbenzimidazole sulfonic acid and salts (Neo Heliopan®Hydro)
3-(4'-trimethylammonium) benzylidene bornan-2-one methyl sulfate
terephthalylidene dibornane sulfonic acid and salts (Mexoryl®SX)
4-t-butyl-4'-methoxydibenzoyl methane (avobenzone)/ (Neo Heliopan®357)
β-imidazole-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone 2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopan®MBC)
3-benzylidene-d,l-camphor
4-isopropyl dibenzoyl methane
2,4,6-trianilino-(p-carbo-2'-ethylhexyl-1'-oxy)-1,3,5-triazine
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
N-[(2 and 4)-[2-(oxoborn-3-ylidene)methyl]benzyl]acrylamide polymer
phenol, -(2H-benzotriazol-2-yl)-4-methyl-6-(2-methyl-3 (1,3,3,3-tetramethyl-1-(trimethylsilypoxy)disiloxanyl)propyl) (Mexoryl®XL)
4,4'-[(6-[(4-(1,1-dimethyl)aminocarbonyl)phenylamino]-1,3,5-triazine-2,4-diyl)diimino]-bis-(benzoic acid-2-ethylhexyl ester) (Uvasorb®HEB)
2,2'-methylene bis-(6-(2H-benzotriazol-2-yl)-4-1,1,3,3-tetramethylbutyl)phenol) (Tinosorb®M)
2,4-bis-[4-(2-ethylhexyloxy)-2-hydroxyphenyl]-1,3,5-triazine
benzylidene malonate polysiloxane (Parsol®SLX)
glyceryl ethylhexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(1,3,5-triazine-2,4,6-triyltriimino)-tris-benzoic acid tris(2-ethylhexyl ester) (Uvinul®T150)
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1,1,1',3'5',5',5'-heptamethylsiloxy-2"-methylpropyloxy)-2-hydroxy}phenyl]-6-(4-methoxyphenyl)-1,3,5-triazine
2-(4-diethylamino-2-hydroxybenzoyl)benzoic acid hexyl ester (Uvinul® A Plus)
indanylidene compounds in accordance with DE 100 55 940 (=WO 02/38537)

UV absorbers which are particularly suitable for combining are
p-aminobenzoic acid
3-(4'-trimethylammonium)benzylidene bornan-2-one methyl sulfate
salicylic acid homomethyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilypoxy)disiloxanyl)propyl) (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-d,l-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds in accordance with DE 100 55 940 (=WO 02/38537)

Advantageous inorganic light protection pigments are finely dispersed metal oxides and metal salts, for example titanium dioxides, zinc oxide (ZnO), iron oxides (e.g. $Fe_2O_3$), aluminium oxide ($Al_2O_3$); cerium oxides (e.g. $Ce_2O_3$), manganese oxides (e.g. MnO), zirconium oxide ($ZrO_2$), silicon oxide ($SiO_2$) silicates (talc), mixed oxides of the corresponding metals and mixtures of such oxides, barium sulfate and zinc stearate. Pigments based on $TiO_2$ or zinc oxide are particularly preferred. In preferred embodiments the particles have an average diameter of less than 100 nm, preferably between 5 and 50 nm and particularly preferably between 15 and 30 nm. They can have a spherical form, but such particles having an ellipsoid form or other form deviating from the spherical shape can also be used. The pigments can also be surface treated, i.e. hydrophilised or hydrophobed. Typical examples are coated titanium dioxides, such as e.g. titanium dioxide T 805 (Degussa) or Eusolex® T2000 (Merck) or coated zinc oxide, such as e.g. zinc oxide NDM. Suitable hydrophobic coating agents are above all silicones and especially trialkoxyoctyl silanes or simethicones. So-called micropigments or nanopigments are preferably used in sunscreens. Zinc micro- or nano-pigments are preferably used.

The total amount of inorganic pigments, particularly hydrophobic inorganic micro-pigments, in the finished cosmetic or dermatological formulations is advantageously in the range from 0.1 to 30 wt. %, preferably 0.1 to 10.0, in particular 0.5 to 6.0 wt. %, based on the total weight of the formulations.

Preparations containing blackberry leaf extract can, as mentioned above, particularly advantageously contain antioxidants, wherein all antioxidants that are suitable for or commonly used for cosmetic and/or dermatological applications can be used. The antioxidants are advantageously selected from the group consisting of amino acids (e.g. glycine, histidine, tyrosine, tryptophane) and derivatives thereof, imidazoles (e.g. urocanic acid) and derivatives thereof, peptides such as D, L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propyl thiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and the salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very small compatible doses, also (metal) chelators, e.g. α-hydroxy fatty acids, palmitic acid, phytic acid, lactoferrin, α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives thereof (e.g. vitamin E acetate), vitamin A and derivatives thereof (vitamin A palmitate) as well as coniferyl benzoate of benzoic resin, rutic acid and derivatives thereof, α-glucosyl rutin, quercetin and derivatives thereof, rosemarinic acid, carnosol, carnosolic acid, resveratrol, ferulic acid and derivatives thereof, furfurylidene glucitol, butyl hydroxytoluene, butyl hydroxyanisole, nordihydroguaiacic resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenium methionine), stilbenes and derivatives thereof (e.g. stilbene oxide, trans-stilbene oxide) along with derivatives (salts, esters, ethers, sugars, nucleotides, nucleosides, peptides and lipids) of these cited active ingredients or extracts or fractions of plants having an antioxidant effect, such as e.g. green tea, rooibos, honeybush, grape, rosemary, sage, melissa, thyme, lavender, olive, oats, cocoa, ginkgo, ginseng, liquorice, honeysuckle, sophora, pueraria, pinus, citrus, Phyllanthus emblica or St. John's wort.

Preferred cosmetic, oral hygiene and/or pharmaceutical preparations containing blackberry leaf extract also contain one or more vitamins and/or vitamin precursors, wherein all suitable or common vitamins and vitamin precursors for cosmetic and/or dermatological applications can be used. These include in particular vitamins and vitamin precursors such as tocopherols, vitamin A, niacin and niacinamide, other B-complex vitamins, in particular biotin and vitamin C, panthenol and derivatives thereof, particularly the esters and ethers of panthenol and cationically derivatised panthenols such as e.g. panthenol triacetate, panthenol monoethyl ether and the monoacetate thereof as well as cationic panthenol derivatives.

A combination with (metal) chelators can also be advantageous in some preparations. (Metal) chelators which are preferably to be used here are α-hydroxy fatty acids, phytic acid, lactoferrin, α-hydroxy acids such as e.g. citric acid, lactic acid and malic acid as well as humic acids, bile acids, bile extracts, bilirubin, biliverdin and EDTA, EGTA and derivatives thereof.

Cosmetic preparations containing blackberry leaf extract that are preferred according to the invention can also contain further anti-inflammatory active ingredients and/or active ingredients relieving reddening and/or itching. All anti-inflammatory active ingredients or active ingredients relieving reddening and/or itching which are suitable for or commonly used for cosmetic and/or dermatological applications can be used here. Steroidal anti-inflammatory substances of the corticosteroid type, such as e.g. hydrocortisone, dexamethasone, dexamethasone phosphate, methyl prednisolone or cortisone, or other steroidal anti-inflammatories are advantageously used as anti-inflammatory active ingredients or active ingredients relieving reddening and/or itching. Non-steroidal anti-inflammatories can also be used, such as for example oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Alternatively, natural anti-inflammatory substances or substances to relieve reddening and/or itching can be used. Plant extracts, special highly active plant extract fractions and highly pure active substances isolated from plant extracts can be used. Particularly preferred are extracts, fractions and active substances from camomile, aloe vera, commiphora species, rubia species, willow, willowherb, oats, calendula, arnica, St. John's wort, honeysuckle, rosemary, *Passiflora incarnata*, witch hazel as well as pure substances such as inter alia bisabolol, apigenin, apigenin-7-glucoside, rosemarinic acid, boswellic acid, phytosterols, glycyrrhizinic acid, glabridin or licochalcone A. The formulations containing blackberry leaf extract can also contain mixtures of two or more anti-inflammatory active ingredients.

Particularly preferred for use within the meaning of the invention are bisabolol, boswellic acid, and extracts and isolated highly pure active ingredients obtained from oats and echinacea, wherein α-bisabolol and extracts and isolated highly pure active ingredients obtained from oats are preferred in particular.

The amount of anti-irritants (one or more compounds) in the preparations according to the invention is preferably 0.0001 to 20 wt. %, particularly preferably 0.0001 to 10 wt. %, in particular 0.001 to 5 wt. %, based on the total weight of the preparation.

Blackberry leaf extract can advantageously be used in combination with (i.e. in particular also mixed with) skin-lightening active ingredients. All skin-lightening active ingredients that are suitable for or commonly used for cosmetic and/or dermatological applications can be used here according to the invention. Advantageous skin-lightening active ingredients in this respect are kojic acid (5-hydroxy-2-hydroxymethyl-4-pyranone), kojic acid derivatives e.g. kojic acid dipalmitate, arbutin, ascorbic acid, ascorbic acid derivatives, hydroquinone, hydroquinone derivatives, resorcinol, sulfur-containing molecules such as e.g. glutathione or cysteine alpha-hydroxy acids (e.g. citric acid, lactic acid, malic acid) and derivatives thereof, chromone derivatives such as aloesin, N-acetyl tyrosine and derivatives, undecenoyl phenylalanine, gluconic acid, 4-alkyl resorcinols, vinyl and ethyl guiacol, inhibitors of nitrogen oxide synthesis, such as e.g. L-nitroarginine and derivatives thereof, 2,7-dinitroindazole or thiocitrulline, metal chelators (e.g. α-hydroxy fatty acids, palmitic acid, phytic acid, lactoferrin, humic acid, bile acid, bile extracts, biliverdin, EDTA, EGTA and derivatives thereof), triterpenes such as lupeol or maslinic acid, flavonoids, retinoids, soya milk, serine protease inhibitors or lipoic acid or other synthetic or natural active ingredients for skin and hair lightening, wherein the latter can also be used in the form of an extract from plants, such as e.g. bearberry extract, rice extract, liquorice root extract or constituents concentrated therefrom, such as glabridin or licochalcone A, artocarpus extract, extract from rumex and ramulus species, extracts from pine species (pinus) and extracts from vitis species or stilbene derivatives concentrated therefrom, extract of saxifrage, mulberry, scutelleria or/and grapes.

The formulations according to the invention can preferably also contain other active ingredients which stimulate skin and hair tinting or lightening by chemical or natural means. A more rapid action based on synergistic effects is achieved in this way. Particularly preferred here are substrates or substrate analogues of tyrosinase such as L-tyrosine, L-DOPA or L-dihydroxyphenylalanine, stimulators of tyrosinase activity or expression such as theophylline, caffeine, proopiomelanocortin peptides such as ACTH, alpha-MSH, peptide analogues thereof and other substances which bind to the melanocortin receptor, purines, pyrimidines, folic acid, phenylalanine derivatives such as e.g. undecylenoyl phenylalanine, diacylglycerols, aliphatic or cyclic diols, psoralens, prostaglandins and analogues thereof, activators of adenylate cyclase and compounds which activate the transfer of melanosomes into keratinocytes such as serine proteases or agonists of the PAR-2 receptor, extracts of plants and plant parts of the chrysanthemum species, walnut extracts, erythrulose and dihydroxyacetone.

Blackberry leaf extract can advantageously also be used in combination with cooling agents. Examples of cooling agents which can be cited are: l-menthol, menthone glycerol acetal, methyl lactate, substituted menthyl-3-carboxylic acid amides (e.g. menthyl-3-carboxylic acid-N-ethylamide), 2-isopropyl-N-2,3-trimethyl butanamide, substituted cyclohexane carboxylic acid amides, 3-menthoxypropane-1,2-diol, 2-hydroxyethyl menthyl carbonate, 2-hydroxypropyl menthyl carbonate, N-acetyl glycine menthyl ester, menthyl hydroxycarboxylic acid esters (e.g. menthyl-3-hydroxybutyrate), monomenthyl succinate, 2-mercaptocyclodecanone, menthyl-2-pyrrolidin-5-one carboxylate.

Blackberry leaf extract can likewise advantageously be used in combination with insect repellents such as e.g. DEET, IR 3225, Dragorepel (Symrise GmbH & Co. KG).

Blackberry leaf extract can furthermore advantageously be used in combination with hair growth inhibitors such as, for example, soya milk, soya protein, soya protein hydrolysate or extracts of plants and plant parts from *Sanguisorba officinalis, Calendula officinalis, Hamamelis virginiana, Arnica montana, Salix alba, Hypericum perforatum, Chondrus* species, *Gloiopeltis* species, *Ceramium* species, *Durvillea* species, plants of the leguminosae, solanaceae, graminae or cucurbitaceae families.

In numerous cases blackberry leaf extract can advantageously also be used in combination with osmolytes such as quaternary amines, amino acids and polyols. Examples of osmolytes which can be cited are: substances from the group of sugar alcohols (myo-inositol, mannitol, sorbitol), taurin, choline, betaine, betaine glycine, phosphorylcholine, glycerophosphorylcholines, glutamine, a-alanine, glutamate, aspartate or proline, as well as their precursors such as glucose, glucose polymers, phosphatidylcholine, phosphatidylinositol, inorganic phosphates, proteins, peptides and polyamine acids.

Blackberry leaf extract can likewise advantageously be used in combination with hair care agents and anti-dandruff active ingredients (e.g. climbazole, ketoconazole, piroctone oleamine, zinc pyrithione).

Blackberry leaf extract can also advantageously be used in many cases in combination with one or more preservatives. Preservatives chosen here are preferably those such as benzoic acid, esters and salts thereof, propionic acid and salts thereof, salicylic acid and salts thereof, 2,4-hexadienoic acid (sorbic acid) and salts thereof, formaldehyde and paraformaldehyde, 2-hydroxybiphenyl ether and salts thereof, 2-zinc sulfidopyridine-N-oxide, inorganic sulfites and bisulfites, sodium iodate, chlorobutanol, 4-ethyl mercury(II)-5-amino-1,3-bis(2-hydroxybenzoic acid, salts and esters thereof, dehydracetic acid, formic acid, 1,6-bis(4-amidino-2-bromophenoxy)-n-hexane and salts thereof, the sodium salt of ethyl mercury(II)-thiosalicylic acid, phenyl mercury and salts thereof, 10-undecenoic acid and salts thereof, 5-amino-1,3-bis(2-ethylhexyl)-5-methyl-hexahydropyrimidine, 5-bromo-5-nitro-1,3-dioxan, 2-bromo-2-nitro-1,3-propanediol, 2,4-dichlorobenzyl alcohol, N-(4-chlorophenyl)-N'-(3,4-dichlorophenyl)urea, 4-chloro-m-cresol, 2,4,4'-trichloro-2'-hydroxydiphenyl ether, 4-chloro-3,5-dimethyl phenol, 1,1'-methylene-bis(3-(1-hydroxymethyl-2,4-dioximidazolidin-5-yl)urea), poly(hexamethylene diguanide)hydrochloride, 2-phenoxyethanol, hexamethylene tetramine, 1-(3-chloroallyl)-3,5,7-triaza-1-azoniaadamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidinedione, benzyl alcohol, octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl-($C_{12}$-$C_{22}$)-trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethyl urea, 1,6-bis(4-amidinophenoxy)-n-hexane and salts thereof, glutaraldehyde, 5-ethyl-1-aza-3,7-dioxabicyclo(3.3.0)octane, 3-(4-chlorophenoxy)-1,2-propanediol, hyamine, alkyl-($C_8$-$C_{18}$)-dimethylbenzyl ammonium chloride, alkyl-($C_8$-$C_{18}$)-dimethylbenzyl ammonium bromide, alkyl-($C_8$-$C_{18}$)-dimethylbenzyl ammonium saccharinate, benzyl hemiformal, 3-iodine-2-propinyl butyl carbamate, sodium hydroxymethylamino acetate or sodium hydroxymethylamino acetate.

It is also preferable according to the invention to use blackberry leaf extract in combination with substances which are principally used to inhibit the growth of undesirable microorganisms on or in animal organisms. Worth mentioning in this respect in addition to standard preservatives as further active ingredients are in particular, in addition to the large group of standard antibiotics, the products relevant for cosmetics, such as triclosan, climbazole, octoxyglycerol, octopirox (1-hydroxy-4-methyl-6-(2,4,4-trimethylpentyl)-2(1H)-pyridones, 2-aminoethanol), chitosan, farnesol, glycerol monolaurate, 1,2-decanediol or combinations of the cited substances, which are used inter alia to combat underarm odour, foot odour or dandruff formation.

Blackberry leaf extract can moreover also be used especially advantageously according to the invention in combination with perspiration-inhibiting active ingredients (antiperspirants) to combat body odour. Aluminium salts such as aluminium chloride, aluminium chlorohydrate, nitrate, sulfate, acetate, etc. are used above all as perspiration-inhibiting active ingredients. The use of zinc, magnesium and zirconium compounds can also be advantageous, however. For use in cosmetic and dermatological antiperspirants the aluminium salts and—to a somewhat lesser extent—aluminium/zirconium salt combinations have proved themselves in the main. Also worth mentioning are the partially neutralised and hence more compatible with the skin, but not quite so effective, aluminium hydroxychlorides. Other possible substances in addition to aluminium salts are for example a) protein-precipitating substances such as inter alia formaldehyde, glutaraldehyde, natural and synthetic tannins and trichloroacetic acid, which bring about a surface closure of the sweat glands, b) local anaesthetics (including dilute solutions of e.g. lidocaine, prilocalne or mixtures of such substances), which switch off the sympathic supply to the sweat glands by blocking the peripheral nerves, c) type X, A or Y zeolites which in addition to reducing sweat secretion also act as adsorbing agents for unpleasant odours, and d) botulinus toxin (toxin of the bacterium Chlostridium botulinum), which is also used for hyperhidrosis, a pathologically increased sweat secretion, and whose action is based on an irreversible blocking of the release of the transmitter substance acetyl choline which is relevant for sweat secretion.

Blackberry leaf extract can advantageously be combined in cosmetic preparations with cosmetic auxiliary substances which are conventionally used in such preparations, in other words with, for example: perfume oils; antifoaming agents; dyes; pigments which have a colouring effect; thickeners; surface-active substances; emulsifiers; softening substances; moistening and/or moisture-retaining substances; fats; oils; waxes; other conventional constituents of a cosmetic formulation such as alcohols, polyols, polymers, foam stabilisers, electrolytes, organic solvents or silicone derivatives.

In blackberry leaf extract-containing formulations for the topical prophylactic or cosmetic treatment of the skin, a high content of conditioning substances is usually advantageous. According to a preferred embodiment the compositions contain one or more conditioning animal and/or vegetable fats and oils such as olive oil, sunflower oil, refined soya oil, palm oil, sesame oil, rapeseed oil, almond oil, borage oil, evening primrose oil, coconut butter, shea butter, jojoba oil, sperm oil, beef fat, neatsfoot oil and pig fat and optionally other conditioning constituents such as for example fatty alcohols having 8 to 30 C atoms. The fatty alcohols here can be saturated or unsaturated and linear or branched. Examples that can be used include decanol, decenol, octanol, octenol, dodecanol, dodecenol, octadienol, decadienol, dodecadienol, oleyl alcohol, ricinol alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well as Guerbet alcohols thereof, wherein the list could be extended almost at will with other alcohols having a related chemical structure. The fatty alcohols preferably come from natural fatty acids, being conventionally produced from the corresponding esters of the fatty acids by reduction. Also usable are fatty alcohol fractions produced by reduction from naturally occurring fats and fatty oils, such as e.g. beef fat, groundnut oil, colza oil, cottonseed oil, soya bean oil, sunflower oil, palm kernel oil, linseed oil, maize oil, castor oil, rapeseed oil, sesame oil, cocoa butter and coconut butter.

Other conditioning substances which combine well according to the invention with blackberry leaf extract include
ceramides, wherein ceramides are understood to be N-acyl sphingosines (fatty acid amides of sphingosine) or synthetic analogues of such lipids (so-called pseudoceramides), which markedly improve the water-retaining capacity of the stratum corneum
phospholipids, for example soya lecithin, egg lecithin and kephalins
vaseline, paraffin and silicone oils; the latter include inter alia dialkyl and alkylaryl siloxanes such as dimethyl polysiloxane and methylphenyl polysiloxane, as well as alkoxylated and quaternised derivatives thereof.

Animal and/or plant protein hydrolysates can advantageously also be added to the blackberry leaf extract. Advantageous in this respect are in particular elastin, collagen, keratin, milk protein, soya protein, oat protein, pea protein, almond protein and wheat protein fractions or corresponding protein hydrolysates, but also condensation products thereof with fatty acids and quaternised protein hydrolysates, the use of plant protein hydrolysates being preferred.

If a cosmetic or dermatological preparation containing blackberry leaf extract is a solution or lotion, the following can advantageously be used as solvents:
water or aqueous solutions;
fatty oils, fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids;
alcohols, diols or polyols having a low C-number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogue products. Mixtures of the aforementioned solvents are used in particular. In the case of alcoholic solvents, water can be an additional constituent.

Cosmetic preparations according to the invention containing blackberry leaf extract can advantageously also contain moisture regulators. The following substances, for example, can be used as moisture regulators (moisturisers): sodium lactate, urea, alcohols, sorbitol, glycerol, diols such as propylene glycol, 1,2-pentanediol, 1,2-hexanediol and 1,2-octanediol, collagen, elastin or hyaluronic acid, diacyl adipates, petroleum jelly, ectoine, urocanic acid, lecithin, pantheol, phytanetriol, lycopene, ceramides, cholesterol, glycolipids, chitosan, chondroitin sulfate, polyamino acids and sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosterols, triterpene acids such as betulinic acid or ursolic acid, algal extracts.

In preferred embodiments of the invention cosmetic preparations containing blackberry leaf extract can also contain mono-, di- and oligosaccharides such as, for example, glucose, galactose, fructose, mannose, fruit sugar and lactose.

It is also preferable for cosmetic preparations containing blackberry leaf extract to contain one or more other plant extracts, which are conventionally produced by extraction of the entire plant, but also in individual cases exclusively from flowers and/or leaves, wood, bark or roots of the plant. With regard to the plant extracts which can be used, reference is made in particular to the extracts listed in the table beginning on page 44 of the 3rd edition of the Leitfaden zur Inhaltsstoffdeklaration kosmetischer Mittel, published by the Industrieverband Körperpflegemittel and Waschmittel e.V. (IKW), Frankfurt. Particularly advantageous are the extracts of aloe, witch hazel, algae, oak bark, willowherb, stinging nettle, dead-nettle, butcher's broom, hops, camomile, yarrow, arnica, calendula, burdock, horsetail, whitethorn, rose, lime blossom, liquorice, almond, pine, horse chestnut, sandalwood, juniper, coconut, mango, apricot, orange, lemon, limette, grapefruit, apple, strawberry, raspberry, grape, pomegranate, green tea, rooibos, honeybush, grapefruit seed, kiwi, avocado, cucumber, wheat, oats, barley, sage, thyme, wild thyme, lavender, rosemary, peppermint, melissa, birch, elder, olive, mallow, lady's smock, horsetail, willow bark, restharrow, coltsfoot, marshmallow, henna, ivy, ginseng, ginkgo, pueraria, sophora, honeysuckle, angelica root, cinnamon, lemongrass and ginger root. The extracts from aloe vera, camomile, algae, rosemary, calendula, ginseng, cucumber, sage, stinging nettle, lime blossom, arnica and witch hazel are particularly preferred here. Mixtures of two or more plant extracts can also be used. Water, alcohols and mixtures thereof, inter alia, can be used as extractants to produce the cited plant extracts. Of the alcohols, low alcohols such as ethanol and isopropanol, but also polyhydric alcohols such as ethylene glycol, propylene glycol and butylene glycol, are preferred, both as the sole extractant and in blends with water. The plant extracts can be used in both pure and diluted form.

According to the invention, cosmetic preparations containing blackberry leaf extract can also contain, especially if crystalline or microcrystalline solids, for example inorganic micropigments, are to be incorporated into the preparations, anionic, cationic, non-ionic and/or amphoteric surfactants. Surfactants are amphiphilic substances which can dissolve organic, non-polar substances in water. The hydrophilic components of a surfactant molecule are mostly polar functional groups, for example —$COO^-$, —$OSO_3^{2-}$, —$SO_3^-$, whilst the hydrophobic components are generally non-polar hydrocarbon radicals. Surfactants are generally classified according to the type and charge of the hydrophilic molecule component. There are four different groups:

anionic surfactants,
cationic surfactants,
amphoteric surfactants and
non-ionic surfactants.

Anionic surfactants generally have carboxylate, sulfate or sulfonate groups as functional groups. In aqueous solution they form negatively charged organic ions in the acid or neutral environment. Cationic surfactants are almost exclusively characterised by the presence of a quaternary ammonium group. In aqueous solution they form positively charged organic ions in the acid or neutral environment. Amphoteric surfactants contain both anionic and cationic groups and therefore behave in aqueous solution in the same way as anionic or cationic surfactants, depending on the pH. They have a positive charge in a strongly acid environment and a negative charge in an alkaline environment. In the neutral pH range, by contrast, they are zwitterionic. Polyether chains are typical of non-ionic surfactants. Non-ionic surfactants do not form ions in the aqueous medium.

Anionic surfactants which can advantageously be used are acyl amino acids (and salts thereof), such as acyl glutamates, for example sodium acyl glutamate, di-TEA-palmitoyl aspartate and sodium caprylic/capric glutamate, acyl peptides, for example palmitoyl-hydrolysed milk protein, sodium cocoyl-hydrolysed soya protein and sodium/potassium cocoyl-hydrolysed collagen, sarcosinates, for example myristoyl sarcosin, TEA-lauroyl sarcosinate, sodium lauroyl sarcosinate and sodium cocoyl sarcosinate, taurates, for example sodium lauroyl taurate and sodium methyl cocoyl taurate, acyl lactylates, lauroyl lactylate, caproyl lactylate
alaninates carboxylic acid and derivatives, such as
for example lauric acid, aluminium stearate, magnesium alkanolate and zinc undecylenate, ester carboxylic acids, for example calcium stearoyl lactylate, laureth-6 citrate and sodium PEG-4 lauramide carboxylate, ether carboxylic acids, for example sodium laureth-13 carboxylate and sodium PEG-6 cocamide carboxylate, phosphoric acid esters and salts, such as e.g. DEA-oleth-10-phosphate and dilaureth-4 phosphate, sulfonic acids and salts, such as
acyl isothionates, e.g. sodium/ammonium cocoyl isothionate, alkyl aryl sulfonates, alkyl sulfonates, for example sodium cocomonoglyceride sulfate, sodium $C_{12-14}$ olefin sulfonate, sodium lauryl sulfoacetate and magnesium PEG-3 cocamide sulfate, sulfosuccinates, for example dioctyl sodium sulfosuccinate, disodium laureth sulfosuccinate, disodium lauryl sulfosuccinate and disodium undecylenamido MEA sulfosuccinate and
sulfuric acid esters, such as
alkyl ether sulfate, for example sodium, ammonium, magnesium, MIPA, TIPA laureth sulfate, sodium myreth sulfate and sodium $C_{12-13}$ pareth sulfate, alkyl sulfates, for example sodium, ammonium and TEA lauryl sulfate.

Cationic surfactants which can advantageously be used are
alkyl amines,
alkyl imidazoles,
ethoxylated amines and
quaternary surfactants.
$RNH_2CH_2CH_2COO^-$ (where pH=7)
$RNHCH_2CH_2COO—B^+$ (where pH=12) $B^+$=any cation, e.g. $Na^+$
esterquats Quaternary surfactants contain at least one N atom, which is covalently bonded to 4 alkyl or aryl groups. This leads to a positive charge, regardless of the pH. Alkyl betaine, alkyl amidopropyl betaine and alkyl amidopropyl hydroxysulfaine are advantageous. The cationic surfactants used can also preferably be chosen from the group of quaternary ammonium compounds, in particular benzyl trialkyl ammonium chlorides or bromides, such as benzyl dimethylstearyl ammonium chloride for example, also alkyl trialkyl ammonium salts, for example cetyl trimethyl ammonium chloride or bromide, alkyl dimethyl hydroxyethyl ammonium chlorides or bromides, dialkyl dimethyl ammonium chlorides or bromides, alkyl amide ethyl trimethyl ammonium ether sulfates, alkyl pyridinium salts, for example lauryl or cetyl pyrimidinium chloride, imidazoline derivatives and compounds having a cationic character such as amine oxides, for example alkyl dimethyl amine oxides or alkyl aminoethyl dimethyl amine oxides. Cetyl trimethyl ammonium salts are particularly advantageously used.

Amphoteric surfactants which can advantageously be used are
- acyl/dialkyl ethylene diamine, for example sodium acyl amphoacetate, disodium acyl amphodipropionate, disodium alkyl amphodiacetate, sodium acyl amphohydroxypropyl sulfonate, disodium acyl amphodiacetate and sodium acyl amphopropionate,
- N-alkyl amino acids, for example aminopropyl alkyl glutamide, alkyl aminopropionic acid, sodium alkyl imidodipropionate and lauroamphocarboxyglycinate.

Non-ionic surfactants which can advantageously be used are
- alcohols,
- alkanolamides, such as cocamides MEA/DEA/MIPA,
- amine oxides, such as cocamidopropylamine oxide,
- esters produced by esterification of carboxylic acids with ethylene oxide, glycerol, sorbitan or other alcohols,
- ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides such as lauryl glucoside, decyl glycoside and cocoglycoside.
- sucrose esters, ethers
- polyglycerol esters, diglycerol esters, monoglycerol esters
- methyl glucose esters, esters of hydroxy acids The use of a combination of anionic and/or amphoteric surfactants with one or more non-ionic surfactants is also advantageous.

The surface-active substance can be present in the blackberry leaf extract-containing preparations according to the invention in a concentration of between 1 and 98 wt. %, based on the total weight of the preparations.

Cosmetic or dermatological preparations containing the blackberry leaf extract according to the invention can also be in the form of emulsions.

The oil phase can advantageously be chosen from the following group of substances:
- mineral oils, mineral waxes
- fatty oils, fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids;
- alkyl benzoates;
- silicone oils such as dimethyl polysiloxanes, diethyl polysiloxanes, diphenyl polysiloxanes and mixed forms thereof.

Substances which can advantageously be used are (a) esters of saturated and/or unsaturated branched and/or unbranched alkane carboxylic acids having a chain length of 3 to 30 C atoms and saturated and/or unsaturated, branched and/or unbranched alcohols having a chain length of 3 to 30 C atoms, (b) esters of aromatic carboxylic acids and saturated and/or unsaturated, branched and/or unbranched alcohols having a chain length of 3 to 30 C atoms. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyl decyl stearate, 2-octyl dodecyl palmitate, oleyl oleate, oleyl erucate, erucyl oleate, erucyl erucate and synthetic, semisynthetic and natural mixtures of such esters, e.g. jojoba oil.

The oil phase can also advantageously be chosen from the group consisting of branched and unbranched hydrocarbons and hydrocarbon waxes, silicone oils, dialkyl ethers, the group consisting of saturated or unsaturated, branched or unbranched alcohols, and of fatty acid triglycerides, in particular the triglycerol esters of saturated and/or unsaturated, branched and/or unbranched alkane carboxylic acids having a chain length of 8 to 24, in particular 12 to 18 C atoms. The fatty acid triglycerides can advantageously be chosen from the group comprising synthetic, semisynthetic and natural oils, e.g. olive oil, sunflower oil, soya bean oil, groundnut oil, rapeseed oil, almond oil, palm oil, coconut oil, palm kernel oil and the like. Any blends of such oil and wax components can also advantageously be used. In some cases it is also advantageous to use waxes, for example cetyl palmitate, as the sole lipid component of the oil phase, the oil phase advantageously being chosen from the group consisting of 2-ethylhexyl isostearate, octyl dodecanol, isotridecyl isononanoate, isoeicosane, 2-ethylhexyl cocoate, $C_{12-15}$-alkyl benzoate, caprylic-capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oil phase can advantageously also have a content of cyclic or linear silicone oils or consist entirely of such oils, it being preferable, however, to use an additional content of other oil phase components along with the silicone oil or silicone oils. Cyclomethicone (e.g. decamethyl cyclopentasiloxane) can advantageously be used as the silicone oil. Other silicone oils can also advantageously be used, however, for example undecamethyl cyclotrisiloxane, polydimethyl siloxane and poly(methylphenyl siloxane). Mixtures of cyclomethicone and isotridecyl isononanoate and of cyclomethicone and 2-ethylhexyl isostearate are also particularly advantageous.

The aqueous phase of blackberry leaf extract-containing preparations in the form of an emulsion can advantageously include: alcohols, diols or polyols having a low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, also alcohols having a low C number, e.g. ethanol, isopropanol, 1,2-propanediol, glycerol and in particular one or more thickeners, which can advantageously be chosen from the group comprising silicon dioxide, aluminium silicates, polysaccharides or derivatives thereof, e.g. hyaluronic acid, xanthan gum, hydroxypropyl methyl cellulose, particularly advantageously from the group of polyacrylates, preferably a polyacrylate from the group of so-called carbopols, for example type 980, 981, 1382, 2984, 5984 carbopols, either individually or in combination.

Preparations containing blackberry leaf extract according to the invention and in the form of an emulsion advantageously include one or more emulsifiers. O/W emulsifiers, for example, can advantageously be chosen from the group of polyethoxylated or polypropoxylated or polyethoxylated and polypropoxylated products, e.g.:
- fatty alcohol ethoxylates
- ethoxylated wool wax alcohols,
- polyethylene glycol ethers having the general formula R—O—(—CH$_2$—CH$_2$—O—)$_n$—R',
- fatty acid ethoxylates having the general formula R—COO—(—CH$_2$—CH$_2$—O—)$_n$—H, etherified fatty acid ethoxylates having the general formula R—COO—(—CH$_2$—CH$_2$—O—)$_n$—R', esterified fatty acid ethoxylates having the general formula R—COO—(—CH$_2$—CH$_2$—O—)$_n$—C(O)—R', polyethylene glycol glycerol fatty acid esters
ethoxylated sorbitan esters,
cholesterol ethoxylates
ethoxylated triglycerides
alkyl ether carboxylic acids having the general formula R—COO—(—CH$_2$—CH$_2$—O—)$_n$—OOH, where n represents a number from 5 to 30, polyoxyethylene sorbitol fatty acid esters,
alkyl ether sulfates having the general formula R—O—(—CH$_2$—CH$_2$—O—)$_n$—SO$_3$—H
fatty alcohol propoxylates having the general formula R—O—(—CH$_2$—CH(CH$_3$)—O—)$_n$—H
polypropylene glycol ethers having the general formula R—O—(—CH$_2$—CH(CH$_3$)—O—)$_n$—R' propoxylated wool wax alcohols,
etherified fatty acid propoxylates R—COO—(—CH$_2$—CH(CH$_3$)—O—)$_n$—R'
esterified fatty acid propoxylates having the general formula R—COO—(—CH$_2$—CH(CH$_3$)—O—)$_n$—C(O)—R' fatty acid propoxylates having the general formula

R—COO—(—CH$_2$—CH(CH$_3$)—O—)$_n$—H, polypropylene glycol glycerol fatty acid esters
propoxylated sorbitan esters,
cholesterol propoxylates
propoxylated triglycerides,
alkyl ether carboxylic acids having the general formula R—O—(—CH$_2$—CH(CH$_3$)—O—)$_n$—CH$_2$—COOH, alkyl ether sulfates or the acids on which these sulfates are based having the general formula R—O—(—CH$_2$—CH(CH$_3$)—O—)$_n$—SO$_3$—H,
fatty alcohol ethoxylates/propoxylates having the general formula R—O—X$_n$—Y$_m$—H
polypropylene glycol ethers having the general formula R—O—X$_n$—Y$_m$—R'
etherified fatty acid propoxylates having the general formula R—COO—X$_n$—Y$_m$—R'
fatty acid ethoxylates/propoxylates having the general formula R—COO—X$_n$—Y$_m$—H.

Particularly advantageously according to the invention the polyethoxylated or polypropoxylated or polyethoxylated and polypropoxylated O/W emulsifiers used are chosen from the group of substances having HLB values of 11 to 18, most particularly advantageously having HLB values of 14.5 to 15.5, if the O/W emulsifiers have saturated R and R' radicals. If the O/W emulsifiers have unsaturated R and/or R' radicals, or if isoalkyl derivatives are present, the preferred HLB value of such emulsifiers can also be lower or higher.

It is advantageous to choose the fatty alcohol ethoxylates from the group of ethoxylated stearyl alcohols, cetyl alcohols, cetyl stearyl alcohols (cetearyl alcohols). Particularly preferred are:

Polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is also advantageous to choose the fatty acid ethoxylates from the following group:

Polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

Sodium laureth-11 carboxylate can advantageously be used as the ethoxylated alkyl ether carboxylic acid or its salt. Sodium laureth 1-4 sulfate can advantageously be used as the alkyl ether sulfate. Polyethylene glycol (30) cholesteryl ether can advantageously be used as the ethoxylated cholesterol derivative. Polyethylene glycol (25) soya sterol has also proved itself.

Polyethylene glycol (60) evening primrose glycerides can advantageously be used as ethoxylated triglycerides.

It is also advantageous to choose the polyethylene glycol glycerol fatty acid esters from the group comprising polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise advantageous to choose the sorbitan esters from the group comprising polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be used as advantageous W/O emulsifiers: fatty alcohols having 8 to 30 carbon atoms, monoglycerol esters of saturated and/or unsaturated, branched and/or unbranched alkane carboxylic acids having a chain length of 8 to 24, in particular 12 to 18 C atoms, diglycerol esters of saturated and/or unsaturated, branched and/or unbranched alkane carboxylic acids having a chain length of 8 to 24, in particular 12 to 18 C atoms, monoglycerol ethers of saturated and/or unsaturated, branched and/or unbranched alcohols having a chain length of 8 to 24, in particular 12 to 18 C atoms, diglycerol ethers of saturated and/or unsaturated, branched and/or unbranched alcohols having a chain length of 8 to 24, in particular 12 to 18 C atoms, propylene glycol esters of saturated and/or unsaturated, branched and/or unbranched alkane carboxylic acids having a chain length of 8 to 24, in particular 12 to 18 C atoms, and sorbitan esters of saturated and/or unsaturated, branched and/or unbranched alkane carboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Surprisingly, the preparations according to the invention containing blackberry leaf extract are especially suitable for the inhibition or reduction of a skin-irritating or inflammatory effect of an irritant substance. Correspondingly, a preparation is also provided according to the invention which contains an irritant substance in an inherently skin-irritating or skin-inflammatory concentration, wherein the preparation also contains a (blackberry leaf extract) preparation or a blackberry leaf extract in accordance with one of the above types, and wherein the concentration of the blackberry leaf extract is sufficient to inhibit or reduce the skin irritation or inflammation caused per se by the irritant substance. The preparation according to the invention is therefore particularly suitable for allowing substances to be applied to the skin which would otherwise not be used because of their skin-irritating or inflammatory or inflammation-promoting effect.

A particular advantage of this preparation according to the invention lies in the fact that owing to the components contained in the preparation according to the invention or in the medicament according to the invention, relatively small amounts and combinations of active ingredients can be used in terms of the skin irritation-preventing effect. This reduces the probability of an allergic reaction, can have cost advantages and can contribute to reducing environmental pollution.

To guard against skin irritation or inflammation, a preparation according to the invention or a medicament according to the invention is applied in an effective amount to the preferably non-irritated skin to be protected.

A further component of the invention is a cosmetic or therapeutic process for the treatment of skin irritation, comprising the following steps:
Provision of a preparation according to the invention or a medicament according to the invention and
Application of the preparation or medicament in an effective amount to irritated skin.

An advantage of this last process according to the invention lies in the fact that the skin-irritating effect of compounds or mixtures of compounds can thus be moderated to such an extent that they become available for uses for which hitherto they were not available. In addition, owing to this last process according to the invention, higher concentrations of skin-irritating compounds and mixtures can be used in applications involving the possibility of skin contact. It is particularly preferable if, owing to this last process according to the invention, the skin-irritating effect of the skin-irritating compound is completely eliminated (i.e. no longer exists) or completely suppressed (i.e. is no longer effective). This last process according to the invention can be used for example to combat the skin-irritating effect of detergents and allergy-triggering substances.

Preferred embodiments and further aspects of the present invention follow from the appended claims and the examples below together with the figures.

EXAMPLE 1

Preparation of Blackberry Leaves Ethanol/water 3:7 Extract 700 g of an ethanol/water 3:7 (m/m) mixture are added to 44 g of dried chopped blackberry leaves and the mixture is stirred for two hours with reflux at a temperature of 80-100° C. After cooling the extraction mixture to room temperature it is filtered through a pleated filter and the clear filtrate is evaporated to dryness under vacuum in a rotary evaporator. 12 g (yield 27.3%) of blackberry leaf extract are obtained.

Characterisation by HPLC fingerprint analysis: Column: YMC ODS-AQ, 5 µm, 150×3 mm with precolumn, temperature: 40° C., flow rate: 0.6 ml/min, acetonitrile/water with 0.1% formic acid gradient, injection volume: 5 µl, detection wavelength: 254 nm. FIG. 1 shows the HPLC diagram obtained.

EXAMPLE 2

Determination of the Total Polyphenol Content

The total polyphenol content is determined photometrically, the content being calculated as catechin equivalents using a catechin calibration curve.

To prepare the EDTA solution, 2.15 g of Titriplex III and 29.0 g of sodium hydroxide are dissolved with distilled water in a 1 l measuring flask. A 0.5-1% solution of the extract to be determined is prepared in distilled water. For the calibration curve catechin solutions of various concentrations in the range from 0.02 to 0.10 mg/ml are prepared in distilled water. 7.5 ml of distilled water, 1.5 ml of the EDTA solution, 1 ml of catechin solution or 1 ml of extract solution and 0.5 ml of Folin-Denis reagent are mixed together and left to stand for 30 minutes at room temperature. In parallel, 1 ml of distilled water is prepared in the same way as a blank control. The absorption of the catechin and extract samples at 760 nm is then measured against the blank control.

A calibration curve is produced from the catechin absorption measurements. The total polyphenol content of the extract is calculated using the equation below:

$$\% \text{ catechin equivalent} = \frac{\text{mg/ml catechin equivalent from calibration curve}}{\text{mg/ml weighed amount of extract}} \times 100$$

EXAMPLE 3

Anti-interleukin-1alpha Assay

Since interleukin-1 alpha (IL-1 alpha) is a central inflammatory mediator in the skin, the inhibiting effect of the blackberry leaf extract on IL-1 alpha biosynthesis in human skin cells (HaCaT keratinocytes) was investigated. The cells are disseminated in a 96-well microtitre plate (MTP) on the previous day. On the day of the experiment, the test substance solutions are applied in medium in three different concentrations as a triple determination and incubated for 60 min at 37° C. and 5% $CO_2$. Cellular IL-1 alpha biosynthesis is then stimulated by the addition of 0.2 µM A23187 calcium ionophore and the solutions are incubated for a further 6 h. The supernatant is drawn off and the cells undergo lysis through the addition of 1% Triton X 100. The IL-1 alpha in the cell lysate is quantified in an ELISA (human IL-1 alpha ELISA kit, EH2IL1A, Endogen).

Result

The results set out below were obtained from two independent experiments. IL-1 alpha inhibition was calculated in comparison to the stimulated control.

| Blackberry extract [%] | IL-1 inhibition [%] | Dexamethasone [µM] | IL-1 inhibition [%] |
|---|---|---|---|
| 0.20% | 39.7% | 1 | 44.7% |
| 0.05% | 27.7% | 0.1 | 37.7% |
| 0.02% | 18.6% | 0.01 | 28.8% |
| 0 | 0.0% | 0 | 0.0% |

With a usage concentration of 0.2% blackberry leaf extract, IL-1 alpha biosynthesis is inhibited by 39.7% as compared with the stimulated control. This inhibition value is comparable with the standard dexamethasone and can therefore be rated as very good.

EXAMPLE 4

Formulations Comprising a Preparation According to the Invention

In Table 1 below
1=skin-lightening day cream O/W
2=skin-soothing lotion with plant extracts O/W
3=after-sun balm
4=body spray
5=sunscreen lotion (O/W), broad-band protection
6=W/O night cream
7=shampoo
8=self-tanning cream
9=barrier repair cream O/W
10=roll-on antiperspirant/deodorant

TABLE 1

| Raw material name (Manufacturer) | INCI | 1 | 2 | 3 | 4 | 5 | 6 | 7 | 8 | 9 | 10 |
|---|---|---|---|---|---|---|---|---|---|---|---|
| | | | | | | WEIGHT % | | | | | |
| SymMatrix (Symrise) | Maltodextrin, *Rubus fruticosus* (blackberry) leaf extract | 0.3 | 0.5 | 0.5 | 0.2 | 0.3 | 1.0 | 0.1 | 0.2 | 1.0 | 0.2 |
| Abil 350 (Degussa-Goldschmidt) | Dimethicone | 0.5 | 2.0 | 1.0 | | | | | 0.5 | 0.5 | |
| Allantoin (Merck) | Allantoin | | 0.2 | 0.1 | | | | | | | |
| *Aloe Vera* Gel Concentrate 10/1 (Symrise) | Water (aqua), *Aloe barbadensis leaf juice* | | | 3.0 | | | 3.0 | | | | |
| Alugel 34 TH (Baerlocher) | Aluminium stearate | | | | | | 1.0 | | | | |
| Aqua-ceramide (Kao) | Cetyloxypropyl glyceryl methoxypropyl myristamide | | 0.1 | | | | | | | | 0.1 |
| Arbutin (Sabinsa) | β-Arbutin | 1.0 | | | | | | | | | |
| Sodium ascorbyl phosphate (EMD Chemicals) | Sodium ascorbyl phosphate | 2.0 | | 1.0 | | | | | | | |
| -(-Alpha-)-Bisabolol, natural (Symrise) | Bisabolol | | 0.4 | 0.3 | | | 0.2 | | | 0.5 | 0.1 |
| Butylene glycol | Butylene glycol | | | 5.0 | | | | | | | |
| Carbopol ETD 2050 (Noveon) | Carbomer | | | | | 0.2 | | | | | |
| Carbopol Ultrez-10 (Noveon) | Carbomer | | 0.1 | | | | | | | | |

TABLE 1-continued

| Raw material name (Manufacturer) | INCI | WEIGHT % | | | | | | | | | |
|---|---|---|---|---|---|---|---|---|---|---|---|
| | | 1 | 2 | 3 | 4 | 5 | 6 | 7 | 8 | 9 | 10 |
| Ceramide 2 (Sederma) | Ceramide 2 | 0.1 | | | | | | | | | |
| Ceramide PC104 (Pacific Corporation) | Hydroxypropyl bispalmitamide MEA | | | | | 0.1 | | | | | |
| Ceramide SL (Sino Lion) | Hydroxyethyl palmityl oxyhydroxypropyl palmitamide | | | | | | | 0.1 | | | |
| Cetiol OE (Cognis) | Dicaprylyl ether | | | | 4.0 | | | | | | |
| Cetiol SB 45 (Cognis) | *Butyrospermum Parkii* (shea butter) | | | | 1.0 | | | | | | |
| Citric Acid 10% sol. | Citric acid | | | | | | | | 0.3 | | |
| Comperlan 100 (Cognis) | Cocamide MEA | | | | | | | | 0.5 | | |
| Dihydroxyacetone (Merck) | Dihydroxyacetone | | | | | | | | | 5.0 | |
| Dow Corning 246 Fluid (Dow Corning) | Cyclohexasiloxane and cyclopentasiloxane | | | | | | 2.0 | | | | |
| Dow Corning 345 Fluid (Dow Corning) | Cyclomethicone | | | | 0.5 | | | | | | |
| D-Panthenol (BASF) | Panthenol | | | 1.0 | | | | | | | |
| Dracorin CE (Symrise) | Glyceryl stearate citrate | 5.0 | | | | | | | 5.0 | 1.5 | |
| Dracorin GMS (Symrise) | Glyceryl stearate | | 2.0 | | | | | | | 2.0 | |
| Dracorin GOC (Symrise) | Glyceryl oleate citrate, caprylic/capric triglyceride | | | | 2.0 | | | | | | |
| Drago-Beta-Glucan (Symrise) | Water (aqua), butylene glycol, glycerine, Avena sativa (oat) kernel extract | 0.3 | | | | | | | | | |
| Dragocid Liquid (Symrise) | Phenoxyethanol, methylparaben, ethylparaben, butylparaben, propylparaben, isobutylparaben | | 0.8 | 0.7 | | 0.7 | 0.8 | | | 0.8 | |
| Dragoderm (Symrise) | Glycerine, *Triticum vulgare* (wheat) gluten, water (aqua) | | | | | | | | 2.0 | | |
| Drago-Oat-Active (Symrise) | Water (aqua), butylene gylcol, *Avena sativa* (oat) kernel extract | | | | 1.0 | | | | | | |
| Dragosan W/O Liquid (Symrise) | Polyglyceryl-3-polyricinoleate, sorbitan isostearate | | | | | | | 1.0 | | | |
| Dragosan W/O P (Symrise) | Sorbitan isostearate, hydrogenated castor oil, ceresin, beeswax (Cera alba) | | | | | | | 6.0 | | | |
| Dragoxat EH (Symrise) | Ethylhexyl ethylhexanoate | 3.0 | 3.0 | | 4.0 | | | | 3.0 | | |
| Dragoxat 89 (Symrise) | Ethylhexyl ethylisononanoate | | | | | | | | | 2.0 | |
| EDETA B powder (BASF) | Tetrasodium EDTA | | | | | | | 0.1 | | | |
| EDETA DB (BASF) | Disodium EDTA | | | | | 0.1 | | | 0.1 | | |
| Emulsiphos (Symrise) | Potassium cetyl phosphate, hydrogenated palm glycerides | | 2.0 | | | 1.5 | | | | 2.0 | |

TABLE 1-continued

| Raw material name (Manufacturer) | INCI | \multicolumn{10}{c}{WEIGHT %} |
| --- | --- | --- | --- | --- | --- | --- | --- | --- | --- | --- | --- |
| | | 1 | 2 | 3 | 4 | 5 | 6 | 7 | 8 | 9 | 10 |
| Ethanol 96% | Ethanol | | | | | | | | 2.0 | | 30.0 |
| Extrapone Green Tea GW (Symrise) | Glycerine, water (aqua), *Camellia sinensis* leaf extract | | 0.2 | | | | | | | | |
| Extrapone Witch Hazel Distillate colorless (Symrise) | Propylene glycol, *Hamamelis virginiana* (witch hazel) water, water (aqua), *Hamamelis virginiana* (witch hazel) extract | | | | | | | 1.0 | | | |
| Extrapone Rosemary GW (Symrise) | Glycerine, water (aqua), *Rosmarinus officinalis* (rosemary) leaf extract | | 0.3 | | | | | | | 0.5 | |
| Farnesol (Symrise) | Farnesol | | | | | | | | | | 0.5 |
| Frescolat ML crist. (Symrise) | Menthyl lactate | | | 0.8 | | | | | | | |
| Genapol LRO liquid (Cognis) | Sodium laureth sulfate | | | | | | | | 37.0 | | |
| Givobio GZN (Seppic) | Zinc gluconate | | | | | | | | | 0.5 | |
| Glycerol 85% | Glycerol | 3.0 | 2.0 | 4.0 | | 4.7 | 2.0 | | 1.5 | 3.0 | |
| Hydrolite-5 (Symrise) | Pentylene glycol | | | | 5.0 | | | | 3.5 | | |
| Hydroviton (Symrise) | Water, glycerine, sodium lactate, TEA lactate, serine, lactic acid, urea, sorbitol, sodium chloride, lauryl diethylene diamino glycine, lauryl aminopropyl glycine, allantoin | | | | | | | | | 1.0 | |
| Ginger $CO_2$ extract (Flavex) | *Zingiber officinale* (ginger) root extract | | 0.004 | 0.003 | | | 0.002 | | | 0.01 | 0.001 |
| Irgasan DP 300 (Ciba Geigy) | Triclosan | | | | | | | | | | 0.3 |
| Isodragol (Symrise) | Triisononanoin | | 2.0 | | | | | | | 3.0 | |
| Isopropyl palmitate (Symrise) | Isopropyl palmitate | 4.0 | | | | | | | 4.0 | | |
| Karion F (Merck) | Sorbitol | | | | | | 2.0 | | | | |
| Keltrol RD (CP-Kelco) | Xanthan gum | 0.2 | 0.1 | | | | | | | | |
| Keltrol T (Danby-Chemie) | Xanthan gum | | | | | 0.2 | | | 0.3 | | |
| Kojic acid (Cosmetochem) | Kojic acid | 1.0 | | | | | | | | | |
| Lanette 16 (Cognis) | Cetyl alcohol | 1.0 | | | | | | | 1.0 | | |
| Lanette O (Cognis) | Cetearyl alcohol | | 3.0 | | | 1.0 | | | | 2.0 | |
| Lara Care A-200 (Rahn) | Galactoarabinan | | | 0.3 | | | | | | | |
| Magnesium chloride (Merck) | Magnesium chloride | | | | | | 0.7 | | | | |
| Merquat 550 (Ondeo Nalco) | Polyquaternium-7 | | | | | | | | 0.5 | | |
| Naringin (Exquim) | 4',5,7-Trihydroxyflavone-7-O-neohesperidoside | | | | | | | | 0.5 | 0.2 | |
| Sodium benzoate | Sodium benzoate | | | | | | | | 0.5 | | |
| Natrosol 250 HHR (Aqualon) | Hydroxyethyl cellulose | | | | | | | | | | 0.3 |
| Neo Heliopan 357 (Symrise) | Butyl methoxy dibenzoylmethane | | | | | 1.0 | | | | | |

TABLE 1-continued

| Raw material name (Manufacturer) | INCI | \multicolumn{10}{c}{WEIGHT %} |||||||||| 
|---|---|---|---|---|---|---|---|---|---|---|---|
| | | 1 | 2 | 3 | 4 | 5 | 6 | 7 | 8 | 9 | 10 |
| Neo Heliopan AP (Symrise) (10% as sodium salt) | Disodium phenyl dibenzimidazole tetrasulfonate | | | | | 10 | | | | | |
| Neo Heliopan AV (Symrise) | Ethylhexyl methoxycinnamate | | | | | 3.0 | | | | | |
| Neo Heliopan Hydro (Symrise) (15% as sodium salt) | Phenylbenzimidazole sulfonic acid | | | | | 6.7 | | | | | |
| Neo Heliopan MBC (Symrise) | 4-Methylbenzylidene camphor | | | | | 1.5 | | | | | |
| Neo Heliopan OS (Symrise) | Ethylhexyl salicylate | | | | | 5.0 | | | | | |
| Neutral oil | Caprylic/capric triglyceride | 6.0 | | | 4.0 | 2.0 | | | 6.0 | 10.0 | |
| Oxynex 2004 (Merck) | BHT | | | | | | 0.1 | | | | |
| Paraffin oil 5 grade E (Parafluid) | Paraffinum liquidum | | | | 4.0 | | | | | | |
| PCL Liquid 100 (Symrise) | Cetearyl ethylhexoate | 3.0 | 5.0 | | 7.0 | | | | | | |
| PCL Solid (Symrise) | Stearyl heptanoate, stearyl caprylate | | 2.0 | | | | | | | | |
| PCL-Liquid (Symrise) | Cetearyl ethylhexanoate, isopropyl myristate | | | | | | | 12.0 | 3.0 | | |
| Pemulen TR-2 (Noveon) | Acrylates/C10-30 alkyl acrylate crosspolymer | | | 0.3 | 0.2 | | | | | | |
| 4-(1-Phenylethyl)1,3-benzenediol | 4-(1-Phenylethyl)1,3-benzenediol | 0.5 | | | | | | | | | |
| Propylene Glycol-1,2 99P GC | Propylene glycol | | 5.0 | | | | | | | | |
| Pseudoceramide 391 | N-(1-hexadecanoyl)-4-hydroxy-L-proline-(1-hexadecyl ester | | 0.1 | | | | | | 0.2 | 0.5 | |
| Retinyl palmitate in oil (DSM Nutritional Products) | Retinyl palmitate | | | | | | 0.2 | | | | |
| Sepigel 305 | Polyacrylamide, C13-14 isoparaffin, laureth-7 | | | | | | | | 1.0 | | |
| Sodium chloride | Sodium chloride | | | | | | | | 1.0 | | |
| Sodium hydroxide (10% sol.) | Sodium hydroxide | | 0.3 | 0.6 | 0.4 | | | | | 0.3 | |
| Solubilizer 611674 (Symrise) | PEG-40 hydrogenated castor oil, trideceth-9, water (aqua) | | | | | | | | | | 2.0 |
| Sunflower oil (Wagner) | Helianthus annuus (sunflower) seed oil | | | | | 5.0 | | | | | |
| Sweet almond oil (Wagner) | Prunus dulcis | | | | | 5.0 | | | | | |
| Symdiol 68 (Symrise) | 1,2-Hexanediol, caprylylglycol | 0.5 | | | | | | | | | |
| Symrise Fragrance | Fragrance | 0.3 | 0.3 | 0.3 | 0.2 | 0.4 | 0.4 | 0.5 | 0.3 | 0.3 | 1.0 |
| Tamasterol (Tama Biochemicals) | Phytosterols | | | | | | | | | 0.3 | |
| Tego Betaine L7 (Degussa) | Cocamidopropyl betaine | | | | | | | 6.0 | | | |
| Tegosoft PC 31 (Degussa) | | | | | | | | | | 0.3 | |
| Tegosoft TN (Degussa) | C12-15 Alkyl benzoate | | | 5.0 | 5.0 | | | | | | |
| Triethanolamine, 99% | Triethanolamine | | | | | 0.5 | | | | | |

TABLE 1-continued

| Raw material name (Manufacturer) | INCI | WEIGHT % | | | | | | | | | |
|---|---|---|---|---|---|---|---|---|---|---|---|
| | | 1 | 2 | 3 | 4 | 5 | 6 | 7 | 8 | 9 | 10 |
| Tocopherol acetate (DSM Nutritional Products) | Tocopheryl acetate | | | 0.5 | | 0.5 | 3.0 | | | 0.3 | |
| Zirkonal L 450 (BK Giulini) | Aluminium zirconium pentachlorohydrate (40% aqueous solution) | | | | | | | | | | 37.0 |
| Water, demineralized | Water (aqua) | to 100 | to 100 | to 100 | to 100 | to 100 | to 100 | to 100 | to 100 | to 100 | to 100 |

Specific Embodiments

A specific embodiment one of the invention is a preparation comprising or consisting of a blackberry leaf extract in a sufficient concentration to inhibit and/or relieve a skin irritation and/or inflammation and/or in a sufficient concentration to reduce the release of an interleukin, the blackberry leaf extract being obtained by or obtainable by a process comprising the following steps:
a) Addition to blackberry leaves of an extractant containing an alcohol selected from the group consisting of methanol, ethanol, n-propanol, iso-propanol and mixtures of two or more of these alcohols, and
b) Extraction of the blackberry leaves with the extractant for up to 72 hours.

A specific embodiment two of the invention is a preparation according to specific embodiment one, wherein the blackberry leaf extract is obtained by or is obtainable by a process further comprising the following steps:
c) Addition to the extract of a solid carrier which is acceptable for pharmaceutical, oral hygiene and/or cosmetic purposes, and
d) Drying of the extract with the added carrier to a residual content of extractant of at most 5 wt. %, based on the total weight of the extract obtained in step d).

A specific embodiment three of the invention is a preparation according to one of the preceding specific embodiments, wherein the alcohol is ethanol.

A specific embodiment four of the invention is a preparation according to one of the preceding specific embodiments, wherein the extractant contains a proportion of at least 15 wt. % of water.

A specific embodiment five of the invention is a medicament for inhibiting and/or relieving a skin irritation and/or inflammation, comprising or consisting of a preparation according to one of specific embodiments one to four in a sufficient concentration to inhibit and/or relieve a skin irritation and/or inflammation.

A specific embodiment six of the invention is a process to inhibit and/or relieve a skin irritation and/or inflammation, comprising the step of applying a preparation according to one of specific embodiments one to four or a medicament according to specific embodiment five to an area of skin to be treated.

A specific embodiment seven of the invention is a process to reduce the release of an interleukin, comprising the step of applying a preparation according to one of specific embodiments one to four or a medicament according to specific embodiment five to an area of skin to be treated.

A specific embodiment eight of the invention is use of a preparation according to one of specific embodiments one to four to inhibit and/or relieve a skin irritation and/or inflammation and/or to reduce the release of an interleukin.

A specific embodiment nine of the invention is a preparation containing an irritant substance in an inherently skin-irritating or skin-inflammatory concentration, further comprising a preparation according to one of specific embodiments one to four, wherein the concentration of the blackberry leaf extract is sufficient to inhibit or reduce the skin irritation or inflammation caused per se by the irritant substance.

A specific embodiment ten of the invention is use of a preparation according to one of specific embodiments one to four to inhibit or reduce a skin-irritating or skin-inflammatory effect of an irritant substance.

The invention claimed is:

1. A process for inhibiting and/or relieving a skin irritation and/or a skin inflammation in a subject in need thereof, comprising applying a preparation to an area of the subject's skin to be treated, wherein said preparation comprises a leaf extract of *Rubus fruticosus* (blackberry) in a sufficient concentration to inhibit and/or relieve the skin irritation and/or skin inflammation and/or in a sufficient concentration to reduce the release of an interleukin, wherein the blackberry leaf extract is obtained by a process comprising:
   a) adding an extractant comprising ethanol and water to blackberry leaves, wherein the ratio of ethanol to water is 2:8 to 8:2: and
   b) extracting the blackberry leaves with the extractant for up to 72 hours, and wherein the preparation does not comprise berries, branches or roots of *Rubus fruticosus*.

2. A process for reducing the release of an interleukin in a subject in need thereof, comprising applying a preparation to an area of the subject's skin to be treated, wherein said preparation comprises a leaf extract of *Rubus fruticosus* (blackberry) in a sufficient concentration to reduce the release of the interleukin and/or to relieve a skin irritation and/or a skin inflammation, wherein the blackberry leaf extract is obtained by or obtainable by a process comprising:
   a) adding an extractant comprising ethanol and water to blackberry leaves, wherein the ratio of ethanol to water is 2:8 to 8:2: and
   b) extracting the blackberry leaves with the extractant for up to 72 hours, and wherein the preparation does not comprise berries, branches or roots of *Rubus fruticosus*.

3. A process for inhibiting and/or relieving a skin irritation and/or a skin inflammation in a subject in need thereof, comprising applying a medicament to an area of skin to be treated, wherein said medicament comprises a leaf extract of *Rubus fruticosus* (blackberry) in a sufficient concentration to inhibit and/or relieve the skin irritation and/or skin inflammation, wherein the blackberry leaf extract is obtained by a process comprising:
  a) adding an extractant comprising ethanol and water to blackberry leaves, wherein the ratio of ethanol to water is 2:8 to 8:2: and
  b) extracting the blackberry leaves with the extractant for up to 72 hours, and wherein the preparation does not comprise berries, branches or roots of *Rubus fruticosus*.

4. A process for reducing the release of an interleukin in a subject in need thereof, comprising applying a medicament to an area of the subject's skin wherein said medicament comprises a leaf extract of *Rubus fruticosus* (blackberry) in a sufficient concentration to reduce the release of the interleukin and/or to inhibit and/or relieve a skin irritation and/or a skin inflammation, wherein the blackberry leaf extract is obtained by a process comprising:
  a) adding an extractant comprising ethanol and water to blackberry leaves, wherein the ratio of ethanol to water is 2:8 to 8:2: and
  b) extracting the blackberry leaves with the extractant for up to 72 hours, and wherein the preparation does not comprise berries, branches or roots of *Rubus fruticosus*.

5. The process according to claim 1, wherein the leaf extract is obtained by a process further comprising:
  c) adding a solid carrier, which is acceptable for pharmaceutical, oral hygiene and/or cosmetic purposes, to the extract; and
  d) drying the extract with the added solid carrier until a residual content of extractant, comprising at most 5 wt. % based on the total weight of the extract obtained in step d), is obtained.

6. The process according to claim 2, wherein the leaf extract is obtained by a process further comprising:
  c) adding a solid carrier, which is acceptable for pharmaceutical, oral hygiene and/or cosmetic purposes, to the extract; and
  d) drying the extract with the added solid carrier until a residual content of extractant, comprising at most 5 wt. % based on the total weight of the extract obtained in step d), is obtained.

7. The process according to claim 1, wherein the extractant contains a proportion of at least 15 wt. % of water.

8. The process according to claim 2, wherein the extractant contains a proportion of at least 15 wt. % of water.

* * * * *